United States Patent [19]

Hodorek

[11] Patent Number: 5,358,530
[45] Date of Patent: Oct. 25, 1994

[54] MOBILE BEARING KNEE
[75] Inventor: Robert A. Hodorek, Warsaw, Ind.
[73] Assignee: Zimmer, Inc., Warsaw, Ind.
[21] Appl. No.: 38,302
[22] Filed: Mar. 29, 1993
[51] Int. Cl.5 .............................................. A61F 2/38
[52] U.S. Cl. ................................................... 623/20
[58] Field of Search .............................. 623/16, 18, 20

[56] References Cited

U.S. PATENT DOCUMENTS

| | | | |
|---|---|---|---|
| 4,224,696 | 9/1980 | Murray et al. | 3/1.911 |
| 4,353,136 | 10/1982 | Polyzoides et al. | 3/1.911 |
| 4,568,348 | 2/1986 | Johnson et al. | 623/20 |
| 4,586,933 | 5/1986 | Shoji et al. | 623/20 |
| 4,728,332 | 3/1988 | Albrektsson | 623/20 |
| 4,808,185 | 2/1989 | Penenberg et al. | 623/20 |
| 4,883,488 | 11/1989 | Bloebaum et al. | 62.3/20 |
| 5,047,057 | 9/1991 | Lawes | 623/20 |
| 5,080,675 | 1/1992 | Lawes et al. | 623/20 |
| 5,116,376 | 5/1992 | May | 623/20 |
| 5,171,283 | 12/1992 | Pappas et al. | 623/20 |

FOREIGN PATENT DOCUMENTS

0498586A1 8/1992 European Pat. Off. .

*Primary Examiner*—David Isabella
*Attorney, Agent, or Firm*—Margaret L. Geringer

[57] ABSTRACT

A prosthetic mobile bearing knee 10 including a femoral implant 12 having condyle sections 22 attached to a femur 14 and a tibial tray implant 16 having a plateau 38 attached to a tibia 18. The tibial tray implant 16 has a pair of spaced apart, concavely curved plateau bearing surfaces 40 for cooperation and sliding with convexly curved surfaces 33 on a tibial bearing 20. The tibial tray plateau bearing surfaces 40 are shaped to create a gradually increasing resistance to sliding and rotational movement of the tibial bearing 20. The tibial bearing 20 that interfits between the femoral and tibial tray implants is constructed in one or two portions.

10 Claims, 2 Drawing Sheets

MOBILE BEARING KNEE

FIELD OF THE INVENTION

The present invention relates generally to an artificial knee prosthesis, and more specifically a mobile bearing knee, for the replacement of a natural knee through surgical implantation.

BACKGROUND OF THE INVENTION

In general, a natural knee is formed by the two condyles at the bottom part of the femur, the lower surfaces of which bear upon the correspondingly shaped upper surface plateaus of the tibia. Connections between the portions of the knee are provided by means of ligaments which also provide joint stability and help to absorb stresses applied to the knee. These knee members are normally subjected to relatively large forces in the course of supporting a major portion of the body weight of a person. Movement of a normal knee is very complex and is not simply a pivotal or rotational movement.

There are two main types of prosthetic knees. The first type is an articulated device in which the femoral and tibial prosthetic components are mechanically linked or constrained to each other by means of a hinge therebetween. The second type is an unlinked device which provides articulation between the femoral implant surfaces and the tibial implant surfaces. Some tibial components are made in a single one-piece configuration, while others are made of a separate tibial bearing which mates with a tibial support member or reinforcing tray. With some of these multi-piece tibial components, the tibial bearing is fixedly secured to the tray portion and thus does not move with respect thereto. U.S. Pat. Nos. 5,047,057 and 4,808,185 show such fixedly secured multi-piece tibial components. Other multi-piece tibial components are designed to allow movement between the tibial bearing and the tibial tray and will be referred to as mobile bearing knees. Thus, such mobile bearing knees allow both movement between the bearing and tray, and movement (articulation) between the femoral component and tibial bearing.

An example of a prior art mobile bearing knee is disclosed in European patent application to Walker, Publication No. 498 586 A1. The tibial component of Walker includes a plastic bearing component supported on a metal platform for sliding movement in the anterior-posterior direction. The mating surface between the bearing and the platform has a sagittal curve to it. The curve on this mating surface is in the anterior-posterior direction, while this mating surface is flat in the medial-lateral direction. This structure disclosed in Walker does not allow for gradual stiffening against rotation at the bearing/platform interface when the femoral and tibial components are rotated relative to one another.

Another prior art mobile bearing prosthetic knee is disclosed in U.S. Pat. No. 4,224,696 to Murray et al. The prosthetic knee of Murray includes a tibial implant having a continuous concave spherical surface engaging a meniscal plate. The Murray et al. knee is free to rotate without resistance.

Other examples of mobile bearing knees are disclosed in the following U.S. Pat. Nos.: 5,171,283; 5,080,675; 4,883,488; 4,728,332; 4,586,933; 4,568,348; 4,353,136.

The present invention is directed to a mobile bearing prosthetic knee, wherein it is desired to create a tibial implant with two specially shaped condyle depressions whereby movement and control of the knee is enhanced.

SUMMARY OF THE INVENTION

The present invention provides an improved tibial tray with two elliptical or spherical depressions for receiving a corresponding mobile tibial bearing member or members, capable of providing improved control during knee movement.

Generally, the invention provides a prosthetic knee for implantation in a body including a femoral implant attached to a femur defining a pair of condyle sections while a tibial tray implant, having a plateau facing toward the femoral implant, is attached to the tibia. The tibial tray implant has a pair of spaced apart concavely curved bearing surfaces on the plateau for cooperation with mating convexly curved surfaces on an interfitting tibial bearing. The tibial plateau bearing surfaces are shaped to permit a gradually increasing resistance to sliding and rotational motion of the tibial bearing. The tibial bearing includes a bearing surface for cooperation with the femoral condyle sections on one side, while on the opposite side are disposed a pair of spaced apart convexly curved surfaces for engagement with the tibial plateau. The tibial bearing may be formed in two portions, each portion containing one bearing surface and one convexly curved surface.

In one form of the invention, the tibial bearing is formed from a single portion in which the two convexly curved sections are connected together.

An advantage of the mobile bearing knee of the present invention is that of improved control of knee movement with the two spherical depressions located medially-laterally on the tibial plateau. The two depressions restrict rotational movement between the femoral and tibial components.

Another advantage of the mobile bearing knee of the present invention is that the knee exhibits improved variable resistance to motions in the medial-lateral direction along with rotational movement.

The invention, in one form thereof, provides a prosthetic knee for implantation in a body having a femoral implant defining a pair of condyle sections attached to a femur. A two-part mobile tibial bearing, each portion having a bearing surface, cooperates with the femoral condyle sections, while each tibial bearing portion further includes, on an opposite side of the bearing surfaces, a convexly curved surface.

A tibial tray is attached to the tibia having a plateau facing toward the femoral implant with a pair of spaced apart concavely curved bearing surfaces for cooperation with the convexly curved surfaces of the two-part tibial bearing. The plateau bearing surfaces have a shape which creates a gradual increasing resistance to sliding and rotational movement of the tibial bearing on the plateau.

In one aspect of the previously described form of the invention, the mobile tibial bearing is of a unitary, one-piece construction. This one-part tibial bearing includes a pair of spaced apart, convexly curved surfaces attached together laying in a medial-lateral orientation relative to the body.

In accordance with another aspect of the invention, the bearing surfaces of the tibial bearing have a particular first radius of curvature and the convexly curved surfaces of the tibial bearing have a particular second radius of curvature, the second radius of curvature being larger than the first radius of curvature. Consequently, stability of the tibial bearing upon the tibial plateau is increased.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
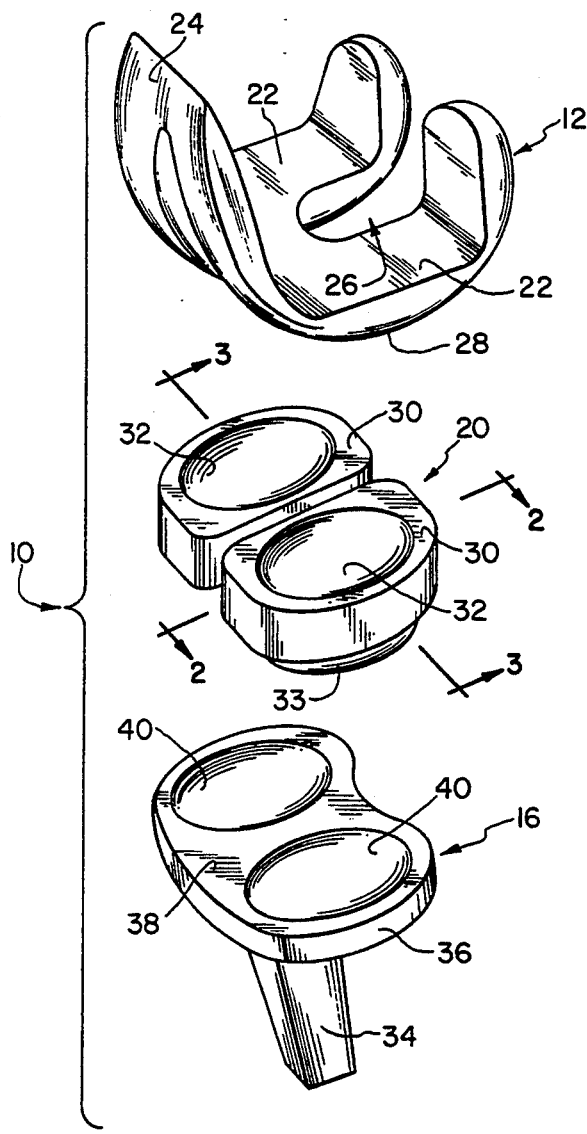
FIG. 1 is an exploded view of the mobile bearing knee of the present invention.
Figure 2:
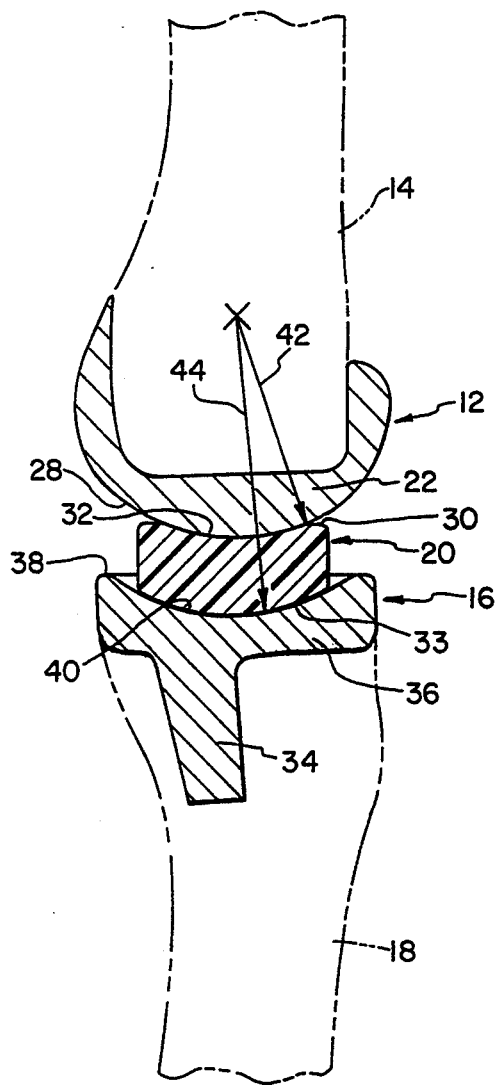
FIG. 2 is a sectional view of the mobile bearing knee of FIG. 1 taken along line 2—2 and viewed in the direction of the arrows while implanted in a patient's leg.

Referring now to FIGS. 1 and 2 there is shown a prosthetic mobile bearing knee 10. In the preferred embodiment, mobile bearing knee 10 comprises a femoral implant 12 which is secured to the patient's femur 14; a tibial tray implant 16 secured to the upper end of the patient's tibia 18; and a two-piece tibial bearing 20 intermediate implants 12 and 16. As is more fully described below, the interface between the tibial tray implant and tibial bearing is defined by cooperating spherically shaped, concave and convex surfaces, respectively, which enables controlled sliding motion along the surfaces between the tibial tray implant and the tibial bearing and, thereby, between both implants 12 and 16.

Referring to FIG. 1, the femoral implant 12 has a somewhat U-shaped configuration and is defined by a pair of spaced apart condyle sections 22 which are interconnected by, and integrally constructed with, a front plate 24 forming a slot or recess 26.

The downwardly facing side of femoral implant 12, particularly condyle sections 22, define convex, compoundly curved condyle surfaces 28 which conform as closely as possible to the shape of the natural condyle surfaces of a normal femur.

Femoral implant 12 is preferably made of a biologically inert cobalt-chrome alloy with the condyle surfaces 28 mirror polished to assure low friction when in sliding interengagement with tibial bearing 20. Alternatively, femoral implant 12 may be constructed of other bio-compatible metals or alloys, such as titanium or any other suitable implantable material.

The tibial bearing 20, of the preferred embodiment, is of a two-piece construction preferably made from ultra-high molecular weight polyethylene, or any other suitable bearing material. Top face 30, of each part of tibial bearing 20, includes a concave, compoundly curved depression 32 (FIG. 1) that forms a bearing surface for a corresponding condyle surface 28 of femoral implant 12. Femoral implant 12 and the two-part tibial bearing 20 are shaped so that sliding motion, which is essentially a pivotal motion, can take place over the full pivotal range of a natural knee.

Two-piece tibial bearing 20 further includes a bottom face 33 on each piece that is formed in a convex, compoundly curved shape to correspond to tibial tray implant 16 described below.

The tibial tray implant 16 may be of a generally T-shaped configuration defined by a downwardly extending, tapered stem 34 and a plate member 36 which replaces the natural tibial plateau of tibia 18 (FIG. 2). Alternatively, the plate member 36 may not include such a depending stem 34, but may include short pegs or other stabilizing means (not shown).

As is the case with femoral implant 12, tibial tray implant 16 is of a uniform one-piece construction made from a biologically inert, high strength metal such as a cobalt-chrome alloy. Alternatively, any bio-compatible material may be used if it can withstand the stress encountered by the joint.

Plate member 36 includes a top surface or plateau 38 that faces upwardly in the direction of femoral implant 12. Plateau 38 includes a pair of spaced apart, concave, compoundly curved depressions 40 in plateau 38. These depressions 40 create a pair of bearing surfaces for cooperation with a respective bottom face 33 of the two-piece tibial bearing 20.

Figure 6:
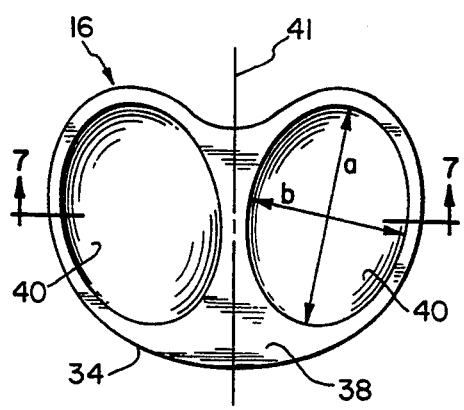
FIG. 6 is a top plan view of the tibial implant of the present invention.
Figure 7:
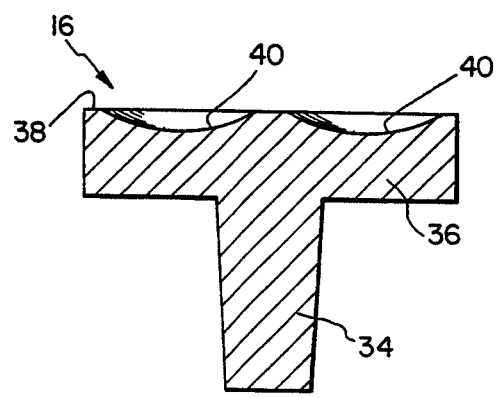
FIG. 7 is a sectional view of the tibial tray of the present invention taken along line 7—7 of FIG. 6 and viewed in the direction of the arrows.

As shown in FIG. 6, plateau 38 is generally formed flat with the two concavely curved bearing surfaces or depressions 40 formed therein. The depressions 40 are dish-shaped and located along the medial-lateral axis.

Depressions 40 are dish-shaped including a major axis A with a minor axis B such that the depressions 40 are elliptical in plan view (FIG. 6).

As shown in FIG. 6, plateau 38 is shown with a bisecting anterior-posterior axis line 41. The major axis A of each of depressions 40 may be nonparallel to the anterior-posterior axis line 41 as shown in FIG. 6. The end point of axis A closest to the anterior side of plateau 38 is nearer to axis line 41 than the other end point. The orientation and nonparallelism of the major axis A to anterior-posterior line 41 permits greater stability of the knee joint, such that each side of tibial bearing 20 and femoral implant 12 are prevented from freely rotating relative to plateau 38. Alternatively, the major axis A may also be parallel (not shown) to axis line 41 which would still provide stability for the knee joint.

Depressions 40, acting with tibial bearing 20, gradually increase resistance to rotation of plate 20 relative plateau 38 as they rotate relative to each other away from center line 41.

Figure 5:
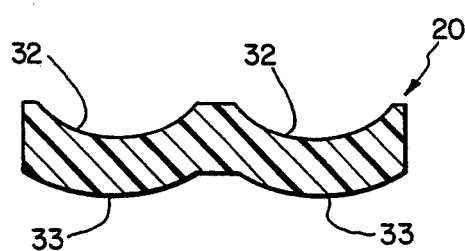
FIG. 5 is a sectional view of the tibial bearing of FIG. 4 taken along line 5—5 and viewed in the direction of the arrows.
Figure 3:
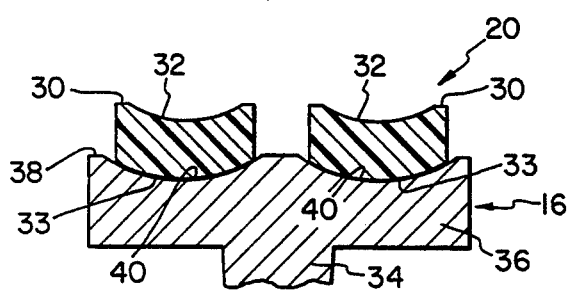
FIG. 3 is a partial sectional view of the mobile bearing knee of FIG. 1 taken along line 3—3 and viewed in the direction of the arrows.

The bottom surface 33 of either the two-part tibial bearing as shown in FIG. 3 or the one-piece alternate embodiment tibial bearing as shown in FIG. 5 substantially interfits with depressions 40 in plateau 38. This interfitting permits a large transfer of load from the patient's body to the femoral implant 12 and then through tibial bearing 20 and tibial tray implant 16. The shape of tibial bearing 20 (in either the two-piece or one-piece form) insures contact of convexly curved surfaces 33 of tibial bearing 20 with depressions 40 of tibial tray 16 at all times. Constant interference and sliding of tibial bearing 20, along with the particular shape of plateau 38 and depressions 40 control relative movement within mobile bearing knee 10.

Sloping sides of bottom surface 33 and the change of curvature of depressions 40 near their edges prevent tibial bearing 20 from sliding too far away from their center equilibrium position.

When under load, tibial bearing 20 will attempt to locate itself centrally within depressions 40 based upon the shape of bottom surface 33. As the patient attempts to move the leg and flex mobile bearing knee 10, tibial bearing 20 and particularly bottom surface 33 will slide along depressions 40. The curvature of depressions 40, along with their relative positions, and the load engaging the knee structure will gradually increase the force necessary for tibial bearing 20 to move out from its central position within depressions 40. In other words, the further tibial bearing 20 and bottom surface 33 moves from its central neutral position within depressions 40, the more force is necessary to slide tibial bearing 20 relative plateau 38.

Based on the relative dimensions of the major axis A and minor axis B of depressions 40, the particular force necessary to move tibial bearing 20 along with the controlling force generated by the structure may be controlled. Rotation of tibial bearing 20 relative to plateau 38 is possible to a certain degree, but the location and orientation of depression 40 creates a gradual stiffening effect. The present invention begins to operate rapidly to increase resistance to rotation based upon how far tibial tray implant 16 and tibial bearing 20 are already rotated relative to each other. Combinations of the load, applied from the patient's weight, along with the dimensions of the depressions 40 interfere with tibial bearing bottom surface 33 and create an increasing force between femoral implant 12 and tibial tray implant 16 to prevent rotation.

As shown in FIG. 2, bearing surface 32 on two-piece tibial bearing 20 has a particular radius of curvature 42. Bottom surface 33 of tibial bearing 20, formed into a convexly curved surface, has a particular radius of curvature 44. The radius of curvature 44 of bottom face 33 may be much larger than radius of curvature 42 of top face 32. Alternatively, radius of curvature 44 may be smaller than radius of curvature 42 as long as stability can be maintained between components 12 and 32.

As the radius of curvature 44 gets smaller, more control of movement of knee 10 is created since it is harder for tibial bearing 20 to slide within depressions 40. Preferably, the radius of curvature 44 is larger than the radius of curvature 42 to prevent instability between the interface between femoral implant 12 and tibial bearing top surface 32.

Figure 4:
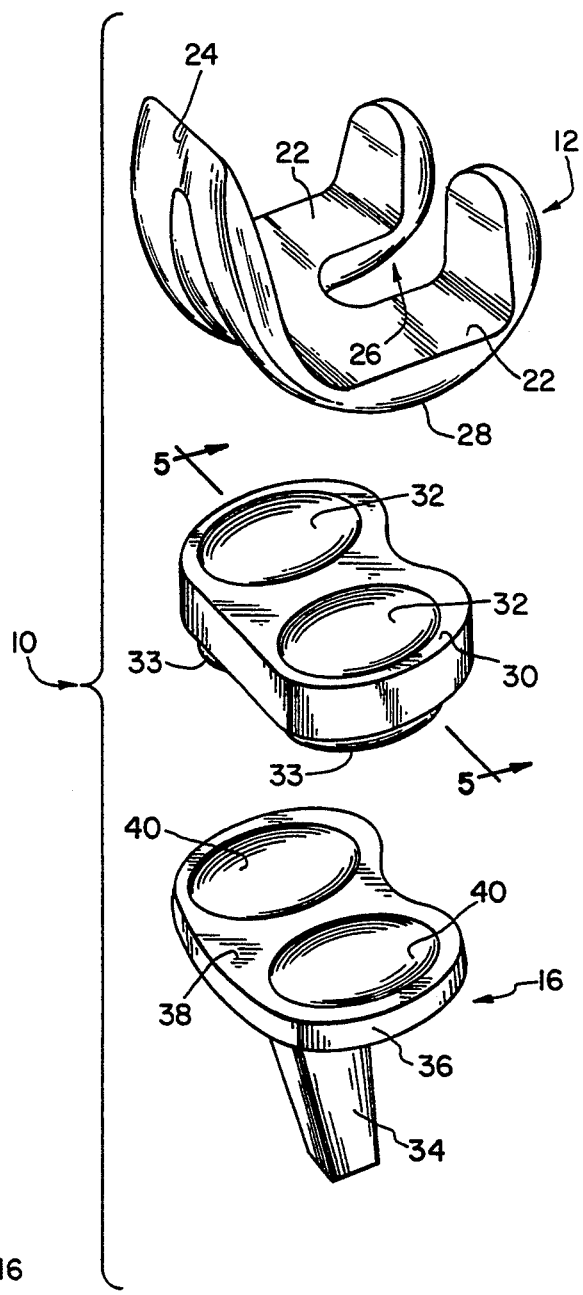
FIG. 4 is an exploded view of an alternate embodiment of the mobile bearing knee showing a one-piece tibial bearing.

The present invention also may include an alternate embodiment of tibial bearing 20. A one-piece tibial bearing 20, as shown in FIG. 5, may be utilized as shown in FIG. 4 for control of movement between femoral implant 12 and tibial tray implant 16.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A prosthetic mobile bearing knee for implantation in a leg comprising:
    a femoral implant for attachment to a femur defining a pair of condyle sections;
    a mobile tibial bearing having a top bearing surface for cooperation with said femoral condyle sections, said tibial bearing further including, on a side opposite said top bearing surface, a pair of spaced apart, convexly curved surfaces; and
    a tibial tray implant for attachment to a tibia, said tibial tray implant including a plateau facing toward said femoral implant having a pair of spaced apart, concavely curved bearing surfaces for cooperation with said convexly curved surfaces of said tibial bearing, said plateau bearing surfaces having a shape permitting a gradual increasing resistance to sliding motion of said tibial bearing on said plateau, and wherein said tibial bearing includes two separate independent and unconnected parts, one part medially located and the other part laterally located relative the leg, each said part comprising one said top bearing surface and one said convexly curved surface.

2. The prosthetic knee of claim 1 in which said top bearing surfaces of the tibial bearing have a particular first radius of curvature and said convexly curved surfaces of the tibial bearing have a particular second radius of curvature, said second radius of curvature being larger than said first radius of curvature.

3. A prosthetic mobile bearing knee for implantation in a leg comprising:
    a femoral implant for attachment to a femur defining a pair of spaced apart, convexly curved condyle sections;
    a mobile tibial bearing having a pair of spaced apart, concavely curved top bearing surfaces for receiving said femoral condyle sections, said tibial bearing further including, on a side opposite said top bearing surface, a pair of spaced apart, convexly curved surfaces; and
    a tibial tray implant for attachment to a tibia, said tibial tray implant including a plateau facing toward said femoral implant having a pair of spaced apart, concavely curved plateau bearing surfaces for receiving said convexly curved surfaces of said tibial bearing, said plateau bearing surfaces of said tibial tray implant restricting sliding movement of said tibial bearing in all directions, and wherein said tibial bearing includes two separate independent and unconnected parts, one part medially located and the other part laterally located relative the leg, each said part comprising one said top bearing surface and one said convexly curved surface.

4. The prosthetic knee of claim 3 in which said top bearing surfaces of the tibial bearing have a particular first radius of curvature and said convexly curved surfaces of the tibial bearing have a particular second radius of curvature, said second radius of curvature being larger than said first radius of curvature.

5. The prosthetic knee of claim 3 in which said top bearing surfaces of the tibial bearing have a particular first radius of curvature and said convexly curved surfaces of the tibial bearing have a particular second radius of curvature, said second radius of curvature being smaller than said first radius of curvature.

6. A prosthetic mobile bearing knee for implantation in a leg comprising:
   a femoral implant for attachment to a femur defining a pair of spaced apart, convexly curved condyle sections;
   a mobile tibial bearing having a pair of spaced apart, concavely curved top bearing surfaces for cooperation with said femoral condyle sections, said tibial bearing further including a bottom surface;
   a tibial tray implant for attachment to a tibia, said tibial tray implant including a plateau facing toward the femoral implant, said tibial plateau in sliding contact with said tibial bearing; and
   a rotation reduction means for gradually increasing resistance to rotation of said mobile tibial bearing plate relative said tibial plateau as they rotate relative each other away from a center point of the prosthetic knee, and wherein said rotation reduction means comprises a pair of spaced apart, convexly curved surfaces on said tibial bearing and a pair of corresponding spaced apart, concavely curved plateau bearing surfaces on said tibial tray implant such that during operation of said knee said convexly curved surfaces provide controlled rotation of said tibial bearing relative to said tibial tray implant, and wherein said tibial bearing includes two separate independent and unconnected parts, one part medially located and the other part laterally located relative the body, each part containing one said top bearing surface and one said convexly curved surface.

7. The prosthetic knee of claim 6 in which said top bearing surfaces of the tibial bearing have a particular first radius of curvature and said convexly curved surfaces of the tibial bearing have a particular second radius of curvature, said second radius of curvature being larger than said first radius of curvature.

8. A prosthetic mobile bearing knee for implantation in a leg comprising:
   a femoral implant for attachment to a femur defining a pair of spaced apart, convexly curved condyle sections;
   a mobile tibial bearing having a pair of spaced apart, concavely curved top bearing surfaces for cooperation with said femoral condyle sections, said tibial bearing further including a bottom surface;
   a tibial tray implant for attachment to a tibia, said tibial tray implant including a plateau facing toward the femoral implant, said tibial plateau in sliding contact with said tibial bearing; and
   a rotation reduction means for gradually increasing resistance to rotation of said mobile tibial bearing plate relative said tibial plateau as they rotate relative each other away from a center point of the prosthetic knee, and wherein said rotation reduction means comprises a pair of spaced apart, convexly curved surfaces on said tibial bearing and a pair of corresponding spaced apart, concavely curved plateau bearing surfaces on said tibial tray implant such that during operation of said knee said convexly curved surfaces provide controlled rotation of said tibial bearing relative to said tibial tray implant, and wherein the tibial tray implant comprises an anterior-posterior axis and wherein each plateau bearing surface has a major axis and a smaller minor axis creating a substantially elliptical depression, and wherein the major axis of each plateau bearing surface is nonparallel to the anterior-posterior axis.

9. The prosthetic knee of claim 8 wherein the major axis has an end point which is anteriorly located relative to the body and an oppositely located end, and wherein the anteriorly located end point is nearer to the anterior-posterior axis than the oppositely located end.

10. A prosthetic mobile bearing knee for implantation in a leg comprising:
    a femoral implant for attachment to a femur defining a pair of spaced apart, convexly curved condyle sections;
    a mobile tibial bearing having a pair of spaced apart, concavely curved top bearing surfaces for cooperation with said femoral condyle sections, said tibial bearing further including a bottom surface;
    a tibial tray implant for attachment to a tibia, said tibial tray implant including a plateau facing toward the femoral implant, said tibial plateau in sliding contact with said tibial bearing; and
    a rotation reduction means for gradually increasing resistance to rotation of said mobile tibial bearing plate relative said tibial plateau as they rotate relative each other away from a center point of the prosthetic knee, and wherein said rotation reduction means comprises a pair of spaced apart, convexly curved surfaces on said tibial bearing and a pair of corresponding spaced apart, concavely curved plateau bearing surfaces on said tibial tray implant such that during operation of said knee said convexly curved surfaces provide controlled rotation of said tibial bearing relative to said tibial tray implant, and wherein the tibial tray implant comprises an anterior-posterior axis and wherein each plateau bearing surface has a major axis and a smaller minor axis creating a substantially elliptical depression, and wherein the major axis of each plateau bearing surface is substantially parallel to the anterior-posterior axis.

* * * * *